United States Patent [19]

Trott et al.

[11] Patent Number: 5,154,720
[45] Date of Patent: Oct. 13, 1992

[54] SURGICAL DRILL GUIDE

[75] Inventors: A. Frank Trott, Largo; Bennie W. Gladdish, Jr., Palm Harbor, both of Fla.

[73] Assignee: Linvatec Corporation, Largo, Fla.

[21] Appl. No.: 838,588

[22] Filed: Feb. 19, 1992

[51] Int. Cl.$^5$ .............................. A61F 2/32
[52] U.S. Cl. ............................................ 606/96
[58] Field of Search ............ 606/86, 87, 96, 97, 606/98, 102, 104

[56] References Cited

U.S. PATENT DOCUMENTS

| | | | |
|---|---|---|---|
| 4,159,716 | 7/1979 | Borchers | 606/96 |
| 4,257,411 | 3/1981 | Cho | 606/96 |
| 4,535,768 | 8/1985 | Hourahane | 606/96 |
| 4,570,624 | 2/1986 | Wu | 606/96 |
| 4,708,139 | 11/1987 | Dunbar | 606/96 |
| 4,739,751 | 4/1988 | Sapega | 606/96 |
| 4,781,182 | 11/1988 | Purnell | 606/96 |
| 4,883,048 | 11/1989 | Purnell | 606/96 |
| 4,920,958 | 5/1990 | Walt | 606/96 |
| 4,945,904 | 8/1990 | Bolton | 606/96 |
| 5,026,376 | 6/1991 | Greenberg | 606/96 |

Primary Examiner—Michael A. Brown
Attorney, Agent, or Firm—Gene Warzecha

[57] ABSTRACT

A drill guide is disclosed in which a cylindrical guide tube is secured to a handle so that it may not be easily longitudinally moved in either direction without the user engaging a thumb activated locking mechanism. The cylindrical guide tube passes through a conically tapered cylindrical bore within the drill guide handle and a similarly tapered split collet is interposed concentrically between the exterior of the cylindrical guide tube and the interior of the bore. The collet is provided with a plurality of longitudinally extending lobes which are sufficiently resilient that movement of the collet to its proximal-most position causes the lobes to squeeze inwardly against the cylindrical guide tube. Frictional engagement between the collet lobes and the guide tube prevents the latter from moving until the collet is moved distally to release pressure on the lobes. The collet is normally biased proximally by a leaf spring attached to the drill guide handle and a thumb activated lever is provided to move the leaf spring distally to release pressure on the lobes and unlock the cylindrical guide tube.

7 Claims, 4 Drawing Sheets

SURGICAL DRILL GUIDE

BACKGROUND OF THE INVENTION

1. Field of the Invention

This invention relates generally to surgical instruments and, in particular, to surgical instruments having a plurality of components that are able to be locked together to produce a fixed structure. More particularly, the invention relates to a drill guide in which a cylindrical tube is slidable relative to a handle and is able to be locked to the handle in a selected position.

2. Description of the Prior Art

Drill guides are often used in surgical procedures in order to facilitate "blind" drilling by properly placing a drill relative to adjacent anatomical structures. A drill guide generally has a handle for holding the guide exterior to the body, a probe tip to be placed within the body at a point where one end of a drilled hole is desired and a tube which has its axis aligned to intersect the probe tip and which is slidable relative to the handle so that the distance between the end of the tube and the probe tip is variable. Drill guides are normally used in arthroscopic procedures by placing the probe tip through an arthroscopic portal, placing the tube end against a bone surface, inserting a drill into the tube and drilling through the bone until the drill comes out adjacent the probe tip.

One example of a prior art drill guide is shown in U.S. Pat. No. 4,739,751 (Sapega et al.). This device handle portion having a curved probe tip which is placeable at a specific location and a cylindrical drill guide attached to an arm slidable along the handle. The axis of the cylindrical drill guide intersects with the tip of the curved probe such that when the probe is placed within a joint during an arthroscopic procedure the placement of the cylindrical drill guide on the exterior surface of the bone enables a drill passing through the guide to intersect with the probe tip. Movement of the drill guide relative to the probe tip is a common feature of drill guides and is necessary to vary the distance between these two components to accommodate different bone thicknesses. Sapega et al. disclose that the drill guide arm may be attached to the handle by a ratchet and pawl mechanism to provide stability during drilling.

U.S. Pat. No. 4,708,139 (Dunbar, IV) discloses a similar arthroscopic drill guide which varies from Sapega et al. essentially in the means by which the drill guide arm is secured to the handle. Dunbar, IV shows a threaded knob passing through the handle and the drill guide arm. Rotation of the knob in one direction locks the guide arm on the handle and rotation in the other direction allows the guide arm to slide along the handle.

U.S. Pat. No. 4,920,958 (Walt et al.) discloses yet another drill guide assembly wherein the drill guide tube is locked to one end of an arcuate handle by a U-shaped spring. The drill guide tube is able to be pushed towards the probe tip without releasing the locking mechanism but is not able to be withdrawn without depressing the two legs of the U-shaped clip together.

Yet another known drill guide is manufactured by the assignee of the present invention and is part of the Concept Precise ACL Guide system. The precise tibial guide has a handle to which a probe tip and a drill guide arm are fixedly attached. The drill guide arm has a threaded aperture at its end and the drill guide is threadably secured in this aperture in alignment with the probe tip. A trigger mechanism on the handle releases the threads momentarily to enable the drill guide to be moved quickly longitudinally without rotation. Releasing the trigger engage the threads of the drill guide with threads in the end of the drill guide arm such that continued movement of the drill guide is only possible by rotation.

It has been found that all of the foregoing devices have features which could be improved upon. Most significantly, it has been found desirable to have a drill guide with an easier, single handed operating mechanism for releasing the guide tube to enable it to be moved longitudinally. It has also been found that, once the tube is in place, it is desirable to have a more secure holding device which prevents longitudinal movement of the tube.

SUMMARY OF THE INVENTION

It is accordingly an object of this invention to produce a drill guide in which the guide tube is easily engageable with the handle when desired, but relatively immovable with respect to the handle when in the locked mode.

It is another object of this invention to produce a drill guide in which the guide tube is relatively locked against movement in either direction relative to the handle unless the locking mechanism is positively released by the user.

It is yet another object of this invention to provide a drill guide wherein the locking mechanism by which the guide tub is locked to the handle is easily operable when depressed by a user's thumb.

These and other objects of the invention are achieved by the preferred embodiment described herein which is a surgical instrument having a locking device for locking component parts of the instrument together, the surgical instrument comprising a handle and an elongated cylindrical portion longitudinally slidable within a cylindrical bore of the handle. A split collet having a tapered external surface surrounds the cylindrical portion and is interposed between it and a correspondingly tapered internal surface of the bore. The collet is adapted to be longitudinally movable to a position where its tapered surface is engaged by the tapered surface of the bore. A trigger attached to the collet and the handle is operable by a user's thumb to move the collet distally, out of engagement with the bore internal surface, or proximally, into engagement.

DESCRIPTION OF THE PREFERRED EMBODIMENT

Figure 2:
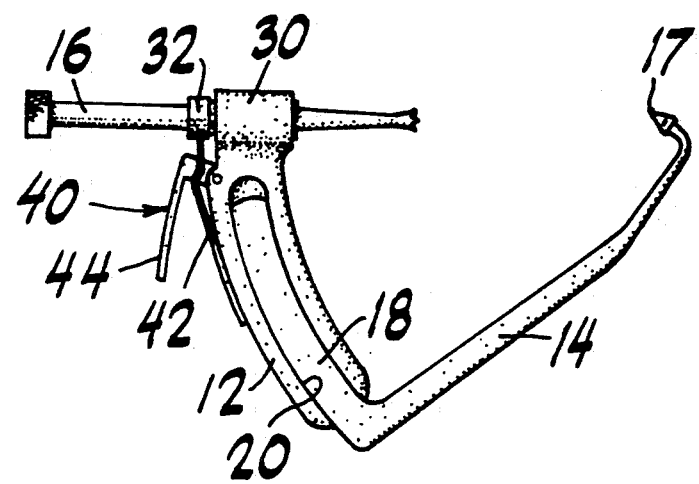
FIG. 2 is a rear elevational view of the tibial drill guide shown in FIG. 1.

Referring now to FIG. there is shown an elevational view of a tibial drill guide 10 having a handle 12, a probe member 14 and a cylindrical drill guide tube 16. The axis of guide tube 16 is aligned with the tip 17 of probe member 14. The rear elevational view of tibial guide 10 is shown in FIG. 2 wherein it may be clearly seen that probe member 14 has an arcuate arm 18 which fits slidably within arcuate slot 20 formed in handle 12. Locking knob 22 secures probe member 14 to handle 12 in a conventional manner.

Figure 3:
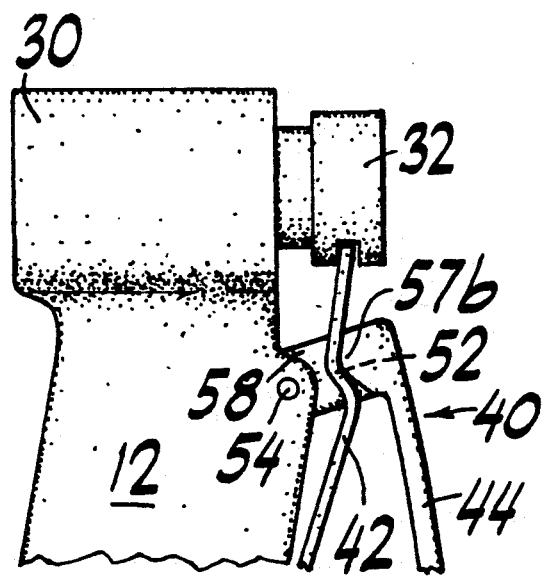
FIG. 3 is an exploded view of a portion of FIG. 1.
Figure 4:
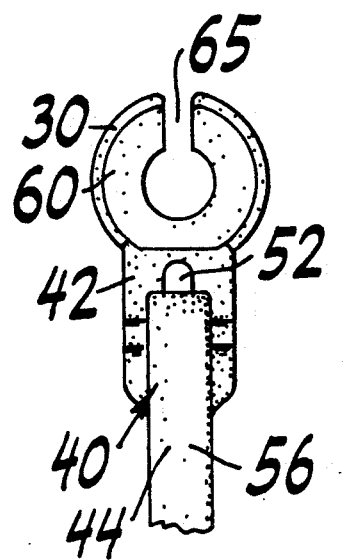
FIG. 4 is a right side elevational view of FIG. 3.
Figure 7:
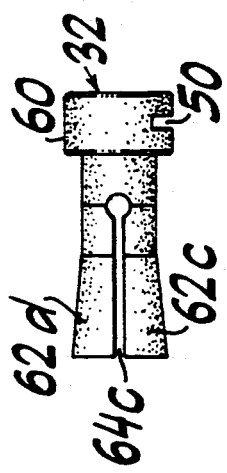
FIG. 7 is a side elevational view of a split collet forming part of this invention.
Figure 8:
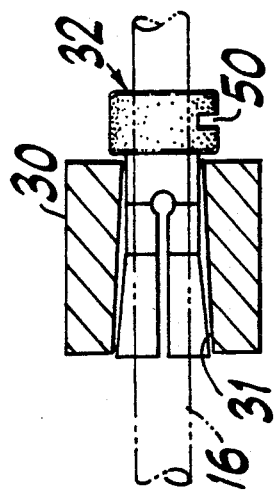
FIG. 8 is a left end view of FIG. 7.
Figure 9:
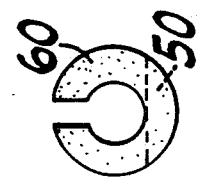
FIG. 9 is a right end view of FIG. 7.

As seen in FIGS. 3 and 4 (in which guide tube 16 is omitted for clarity), the upper end of handle 12 is formed into a cylindrical housing 30 having a tapered interior channel (best seen in FIGS. 12 and 13) within which is received a split collet 32 (best in FIGS. 7, 8 and 9). Cylindrical tube 16 is sized to be received and axially aligned within collet 32 (in its uncompressed state) and housing 30. As will be better understood below, collet 32 is longitudinally movable within the interior channel 31 of housing 30 from a locked position in which collet 32 is at its proximal-most position relative to housing 30 (best seen in FIG. 12) and an unlocked position in which collet 32 is at its distal-most position relative to housing 30 (best see in FIG. 13).

Figure 1:
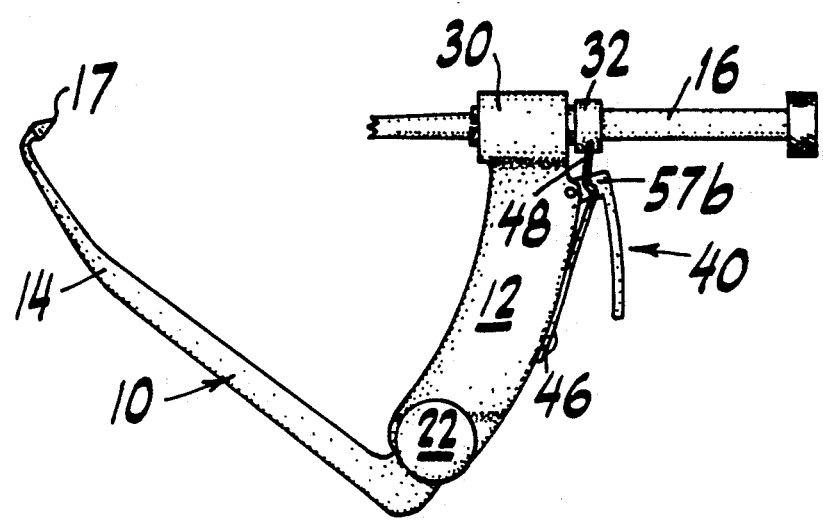
FIG. 1 is an elevational view of a preferred embodiment of the invention in the form of a tibial drill guide.
Figure 10:
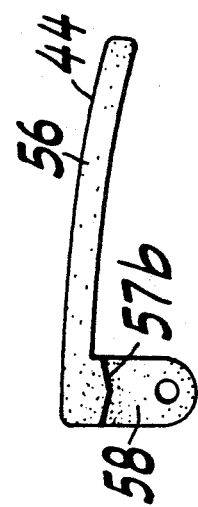
FIG. 10 is a side elevational view of the spring lever forming a part of this invention.
Figure 11:
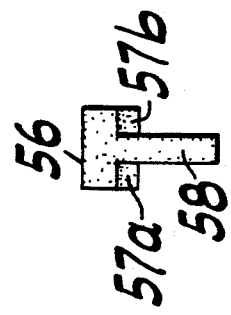
FIG. 11 is a left end view of FIG. 10.
Figure 6:
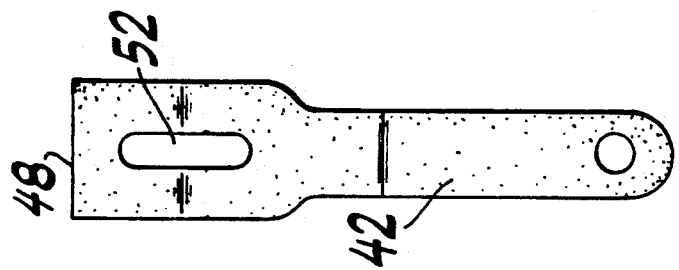
FIG. 6 is a right side elevational view of FIG. 5.
Figure 5:
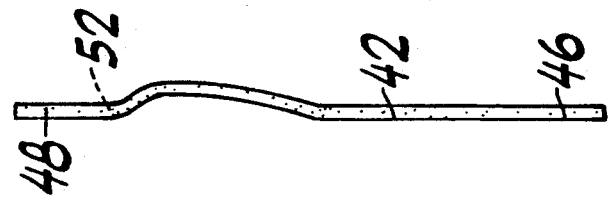
FIG. 5 is a side elevational view of a leaf spring forming a part of this invention.

Movement of collet 32 relative to housing 30 is accomplished by cruciate trigger mechanism 40 which comprises a leaf spring 42 (best seen in FIGS. 5 and 6) and a thumb lever 44 (best seen in FIGS. 1, 10 and 11). The lower end 46 of leaf spring 42 is fixedly secured to handle 12 and the upper end 48 is secured within a receiving channel 50 formed in the head 60 of collet 32 (best seen in FIGS. 3 and 7). It will be understood that collet 32 is normally free to move longitudinally within the internal bore 31 of housing 30 and, by making spring 42 normally biased proximally (i.e. to the right as viewed in FIG. the collet is normally biased proximally as well. Leaf spring 42 has a relatively wide end 48 (best seen in FIGS. 4 and 6) in order to conform the shape of end 48 to the relatively rectangular shape of channel 50.

Leaf spring 42 includes an aperture 52 near end 48, aperture 52 serving to receive thumb lever 44 therethrough. Thumb lever 44 is hingedly connected at 54 to handle 12 and has a relatively wide thumb contacting arm 56, the upper end of which is joined to a relatively narrow hinge arm 58. Arm 56 has a pair of shoulders 57a and 57b adjacent hinge arm 58 and the interaction of the shoulders with the edges of aperture 52 serves to move leaf spring 42 distally as thumb lever 44 is depressed, thus causing end 48 and collet 32 to move distally. Releasing pressure on thumb lever 44 allows the natural bias of spring 42 to move itself and associated parts proximally. It will be understood that the shape of either spring 42 or lever 44 may change depending on the structure of handle 12.

Figure 12:
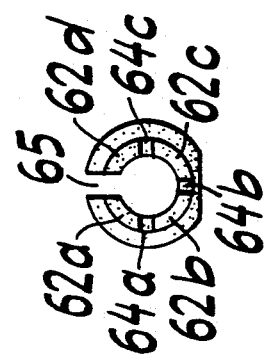
FIG. 12 is a diagrammatic view of the relationship of parts of the invention in the locked mode.
Figure 13:
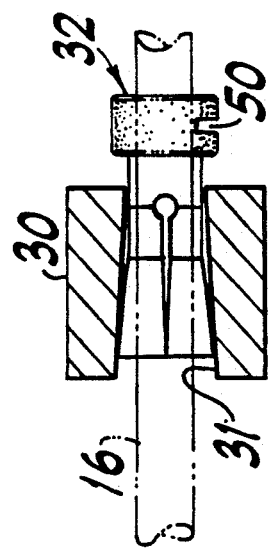
FIG. 13 is a diagrammatic view of the relationship of parts of the invention in the unlocked mode.

Collet 32 has four longitudinally extending fingers or lobes 62a, b, c and d, each of which is arcuately shaped. Three identical channels 64a, b and c separate some of the lobes as shown, and a top channel 65 extends the length of collet 32. As best seen in FIGS. 12 and 13, movement of collet 32 to its proximal-most position relative to housing 30 causes the tapered interior of bore 31 to squeeze the lobes inwardly to frictionally engage tube 16. Movement of collet 32 to its distal-most position relaxes the radially inward pressure and allows the natural resiliency of the lobes to permit tube 16 to slide in either direction.

While the preferred embodiment shows the use of a collet with four tapered lobes, other arrangements may be suitable. For example, any number of lobes may be appropriate; non-tapered surfaces may be used if other means are provided to cam the collet lobes inwardly, etc.

Also, while the invention has been described in terms of a drill guide, it will be understood that other surgical instruments may be adapted to incorporate the principles of the invention.

It will be understood by those skilled in the art that numerous modifications and improvements may be made to the preferred embodiment of the invention described herein without departing from the spirit and scope thereof.

What is claimed is:

1. A surgical instrument comprising a handle and an elongated cylindrical portion longitudinally slidable within a cylindrical bore of said handle, said instrument having a locking device for locking component parts of the surgical instrument together, said surgical instrument comprising:

a collet surrounding part of said cylindrical portion and interposed between same and the internal surface of said bore, said collet adapted to be longitudinally movable and having at least two longitudinally extending lobes the external surfaces of which form a tapered surface;

a tapered interior surface forming the interior of said bore and adapted to be engaged by said collet tapered surface when said collet is moved proximally;

a thumb activated trigger means attached to said handle and adapted to move said collet distally into a first, unlocked position wherein said lobes are not in frictional engagement with said cylindrical portion and proximally into a second, locked position wherein said lobes are urged radially inwardly to lock said cylindrical portion relative to said handle.

2. A surgical instrument according to claim 1 wherein said thumb activated trigger means comprises:

an elongated leaf spring member fixedly secured at one end to said handle and loosely secured at its other end to said collet, said leaf spring adapted to normally bias said collet proximally;

an elongated thumb activated trigger lever hingedly secured at one end to said handle and adapted to have an intermediate portion thereof engageable with said leaf spring, said trigger lever being normally biased proximally by said leaf spring.

3. A surgical instrument according to claim wherein said thumb activated trigger means comprises:

a cruciate trigger structure having first and second elongated members, said first member crossing and engageable with an intermediate portion of said second member, one end of said first member attached to said handle and the other end attached to said collet, one end of said second member attached to said handle and the other end being free such that movement of said free end toward said one end of said first member causes said collet to move longitudinally.

4. A surgical instrument comprising a handle and an elongated cylindrical portion longitudinally slidable within a cylindrical bore of said handle, said instrument having a locking device for locking component parts of the surgical instrument together, said surgical instrument comprising:
- a collet concentrically surrounding part of said cylindrical portion and interposed between same and the internal surface of said bore, said collet adapted to be longitudinally movable between a first position and a second position;
- locking means attached to said collet and adapted to be moved radially inwardly either into or away from abutting, frictional engagement with said cylindrical portion when said collet is moved to said first or second position, respectively;
- means for moving said locking means transversely into said abutting, frictional engagement to lock said cylindrical portion relative to said handle
- means attached to said handle for moving said collet between said first and second positions.

5. A surgical instrument according to claim 4 wherein said locking means is an integral part of said collet and comprises at least two longitudinally extending lobe members circumferentially arranged about the axis of said cylindrical portion, each of said lobe members extending in one direction from the body of said collet and having a free end normally biased away from the surface of said cylindrical portion and adapted to be transversely moved into engagement with said surface to frictionally engage same to thereby restrain longitudinal motion of said cylindrical portion relative to said handle.

6. A surgical instrument according to claim 5 wherein each of said lobes has an arcuately shaped cross-section along a predetermined portion of its length, said arcuate cross-section adapted to engage the cylindrical exterior surface of said cylindrical portion.

7. In a surgical drill guide comprising a handle, a probe member secured to said handle, a guide tube slidably secured within a bore of said handle and aligned with the tip of said probe member, means for locking said guide tube relative to said handle comprising:
- a collet surrounding part of said guide tube and interposed between same and the internal surface of said bore, said collet adapted to be longitudinally movable and having at least two longitudinally extending lobes the external surfaces of which form a tapered surface;
- a tapered interior surface forming the interior of said bore and adapted to be engaged by said collet tapered surface when said collet is moved proximally;
- a thumb activated trigger means attached to said handle and adapted to move said collet distally into a first, unlocked position wherein said lobes are not in frictional engagement with said guide tube and proximally into a second, locked position wherein said lobes are urged radially inwardly to lock said cylindrical portion relative to said handle.

* * * * *

UNITED STATES PATENT AND TRADEMARK OFFICE
CERTIFICATE OF CORRECTION

PATENT NO.  : 5,154,720
DATED       : OCTOBER 13, 1992
INVENTOR(S) : A. FRANK TROTT and BENNIE W. GLADDISH It is certified that error appears in the above-identified patent and that said Letters Patent is hereby corrected as shown below:

```
Col. 1, line 30, after the word "device" insert
       -- includes a --

Col. 2, line 33, please change "tub" to -- tube --

Col. 3, line 8, after "FIG." insert -- 1 -- ;
        line 43, after "FIG." insert -- 1) --
Col. 4:
Claim 3, line 1, after the word "claim" insert
        -- 1 --
```

Signed and Sealed this

Twenty-eighth Day of September, 1993

Attest:

BRUCE LEHMAN

Attesting Officer

Commissioner of Patents and Trademarks